(12) United States Patent
Dyke et al.

(10) Patent No.: US 6,169,090 B1
(45) Date of Patent: Jan. 2, 2001

(54) HETEROCYCLIC COMPOUNDS AND THEIR THERAPEUTIC USE

(75) Inventors: Hazel Joan Dyke; Verity Margaret Sabin; Andrew Sharpe; Alan Findlay Haughan; Christopher Lowe; George Buckley; John Montana, all of Cambridge (GB)

(73) Assignee: Darwin Discovery, Ltd. (GB)

( * ) Notice: Under 35 U.S.C. 154(b), the term of this patent shall be extended for 0 days.

(21) Appl. No.: 09/328,182

(22) Filed: Jun. 8, 1999

(30) Foreign Application Priority Data

Jun. 8, 1998 (GB) .................................. 9812322
Sep. 23, 1998 (GB) .................................. 9820768

(51) Int. Cl.[7] ................. C07D 491/048; A61K 31/44
(52) U.S. Cl. ................. 514/256; 546/116; 544/322; 514/302
(58) Field of Search ..................... 546/116; 514/302, 514/276; 544/322

(56) References Cited

U.S. PATENT DOCUMENTS 4,910,193   3/1990   Buchheit .................. 514/216

FOREIGN PATENT DOCUMENTS

| 0637586 | 8/1994 | (EP) . |
| 9108832 | 4/1997 | (JP) . |
| 10298180 | * 11 1998 | (JP) . |
| 9412461 | 10/1992 | (WO) . |
| 9408962 | 10/1993 | (WO) . |
| 9636638 | 5/1996 | (WO) . |

* cited by examiner

*Primary Examiner*—Mukund J. Shah
*Assistant Examiner*—Hong Liu
(74) *Attorney, Agent, or Firm*—Saliwanchik, Lloyd & Saliwanchik

(57) ABSTRACT

The compound, according to formula (i)

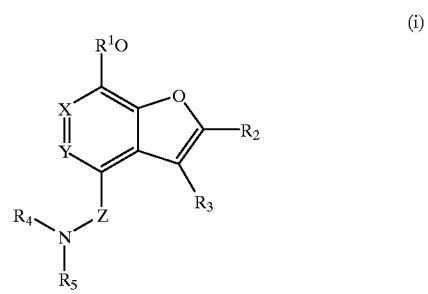

wherein X and Y are independently CH, N or N-oxide, provided that X and Y do not both represent CH;

Z is CO or CS;

$R_1$ is alkyl, optionally substituted with one or more halogens; and $R_2$, $R_3$, $R_4$ and $R_5$ are each various organic groups.

Such compounds have therapeutic utility, via inhibition of phosphodiesterase IV.

13 Claims, No Drawings

HETEROCYCLIC COMPOUNDS AND THEIR THERAPEUTIC USE

FIELD OF THE INVENTION

The present invention relates to novel heterocyclic compounds and to their formulation and use as pharmaceuticals.

BACKGROUND OF THE INVENTION

EP-A-0637586 describes benzofuran derivatives of acetylcholine esterase inhibitors. U.S. Pat. No. 4,910,193 discloses benzofuran amides for the treatment of serotonin-induced gastrointestinal disturbances. WO-A-9408962 discloses benzofuran derivatives as fibrinogen receptor antagonists.

WO-A-9412461 discloses catechol diethers as selective phosphodiesterase (PDE) IV inhibitors. The modes of action of phosphodiesterases and also tumour necrosis factors (TNF), and the therapeutic utilities of inhibitors thereof, are described in WO-A-9636638 and U.S. patent application Ser. No. 07/650,231, the contents of which are incorporated herein by reference. WO-A-9744337 discloses benzofuran carboxamides as PDE IV inhibitors.

SUMMARY OF THE INVENTION

This invention provides novel compounds having therapeutic utility, in particular for the treatment of disease states associated with proteins which mediate cellular activity, for example by inhibiting TNF and/or PDE IV. According to the invention, the compounds are of formula (i):

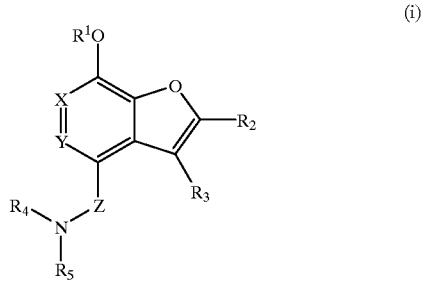

wherein X and Y are independently CH, N or N-oxide, provided that X and Y do not both represent CH;

Z is CO or CS;

$R_1$ is alkyl, optionally substituted with one or more halogens;

$R_2$ is $CF_3$, H, CN, $C(=NOR_9)R_9$, alkyl-$C(=NOR_9)R_O$, $S(O)_pR_6$, $SO_2NR_{12}R_{12}$, $CONR_{12}R_{13}$, $OR_9$, $NR_6R_{15}$; alkyl, cycloalkyl or cycloalkylalkyl optionally substituted with one or more $R_8$; aryl, heteroaryl, arylalkyl or heterocycloalkyl, the aryl/heteroaryl portions of which may be otionally substituted by one or more $R_2$ or alkyl-$R_{10}$ and the alkyl portions of which may be optionally substituted by one or more $R_8$; or heterocyclo or heterocycloalkyl, the heterocyclo portion of which may be optionally substituted by one or more $R_{11}$ or alkyl-$R_{10}$ and the alkyl portion of which may be optionally substituted by one or more $R_3$, $R_3$ is H, alkyl or halogen;

$R_4$ is H or alkyl;

$R_5$ is aryl or heteroaryl, optionally substituted at any position with (one or more) substituents alkyl-$R_{10}$ or $R_7$;

$R_6$ is alkyl, aryl, heteroaryl, cycloalkyl, cycloalkylalkyl, arylalkyl, heteroarylalkyl, heterocyclo or heterocycloalkyl, the cycloalkyl/alkyl portions of which may be optionally substituted with one or more $R_8$, the aryl/heteroaryl portions of which may be optionally substituted with one or more $R_7$ or alkyl-$R_{10}$ and the heterocyclo portions of which may be optionally substituted with one or more $R_{11}$ or alkyl-$R_{10}$;

$R_7$ is alkyl or $R_{17}$;

$R_8$ is carbonyl oxygen (=O) or $R_{10}$;

$R_9$ is H or $R_6$;

$R_{10}$ is $CO_2R_{16}$, $CONR_{12}R_{13}$, $SO_2NR_{12}R_{13}$, OH, $OR_{12}$, CN, $CF_3$, $NR_{12}R_{15}$, $COR_{12}$, $S(O)_7R_{12}$, $NHSO_2CF_3$, $NO_2$, aryl optionally substituted with one or more $R_{18}$, heteroaryl optionally substituted with one or more $R_{18}$, or heterocyclo optionally substituted with one or more $R_{19}$;

$R_{11}$ is carbonyl oxygen, alkyl or $R_{10}$;

$R_{12}$ and $R_{13}$ are the same or different and are H, alkyl, cycloalkyl, aryl, heteroaryl, heterocyclo, cycloalkylalkyl, arylalkyl, heteroarylalkyl, heterocycloalkyl or $NR_{12}R_{13}$ represents a heterocyclic ring, the aryl/heteroaryl portions of which may be optionally substituted with one or more $R_{18}$ and the heterocyclo portions of which may be optionally substituted with one or more $R_{19}$;

$R_{15}$ is H, alkyl, cycloalkyl, aryl, heteroaryl, heterocyclo, cycloalkylalkyl, arylalkyl, heteroarylalkyl, heterocycloalkyl, alkylcarbonyl, alkoxycarbonyl, arylcarbonyl, heteroarylcarbonyl, heterocyclocarbonyl, alkylsulfonyl, arylsulfonyl, heteroarylsulfonyl, heterocyclosulfonyl, the aryl/heteroaryl portions of which may be optionally substituted with one or more $R_{18}$ and the heterocyclo portions of which may be optionally substituted with one or more $R_{19}$, $R_{16}$ is H, alkyl, cycloalkyl, cycloalkylalkyl, arylalkyl, heteroarylalkyl, heterocyclo or heterocycloalkyl;

$R_{17}$ is halogen or $R_{10}$, $R_{18}$ is alkyl, alkoxy, $CF_3$, halogen, CN or $CO_2R_{16}$, $R_{19}$ is alkyl, alkoxy, $CF_3$, arylalkyl, carbonyl oxygen, CN or $COR_2R_{16}$; and p is 0–2;

and N-oxides and pharmaceutically acceptable salts thereof.

This invention provides also a method for mediating or inhibiting the enzymatic activity or catalytic actvity of PDE IV in a mammal in need thereof and for inhibiting the production of TNF in a mammal in need thereof, which comprises administering to said mamnmal an effective amount of a compound of Formula (i) or a pharmaceutically-acceptable salt thereof.

DESCRIPTION OF THE INVENTION

Certain compounds of this invention are preferred. For example, it is preferred that any one or more of the following apply:

$R_1$ is methyl or difluoromethyl;

$R_2$ is alkyl or cycloalkyl optionally substituted with (one or more) $R_8$, aryl or heteroaryl optionally substituted with (one or more) $R_7$ or alkyl-$R_{10}$, or heterocyclo optionally substituted with one or more $R_{11}$ or alkyl-$R_{10}$;

$R_3$ is H;

$R_4$ is H;

R₅ is phenyl, pyridinyl, pyridinyl-N-oxide, pyrimidinyl pyrazolyl, imidazolyl, isoxazolyl, any of which may be substituted at any position with (one or more) substituents $R_7$ (in which $R_7$ is alkyl, $CF_3$, halogen or CN);

X is N and Y is CH or X is CH and Y is N; and

Z is CO.

The compounds of the Examples are particularly preferred.

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically-acceptable inorganic salts such as the sulphate, nitrate, phosphate, borate, hydrochloride and hydrobromide, and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric or geometric form. This invention extends to all tautomeric and geometric forms.

It will be appreciated that the compounds according to the invention can contain one or more asymmetrically substituted carbon atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of another group includes straight and branched chain alkyl groups containing up to 6 atoms. Alkoxy means an alkyl-O-group in which the alkyl group is as previously described, and thioalkyl means an alkyl-S-group. Cycloalkyl includes a non-aromatic cyclic or multicyclic ring system of 3 to 10 carbon atoms. Cycloalkylalkyl means a cycloalkyl-alkyl-group wherein the cycloalkyl and alkyl groups are as previously defined. The cyclic alkyl may optionally be partially unsaturated. Aryl indicates a mono- or multicyclic aromatic radical containing 6 to 10 carbon atoms. Arylalkyl means an aryl-alkyl-group wherein the aryl and alkyl are as described herein. Heteroaryl means a 5 to 10 membered aromatic monocyclic or multicyclic hydrocarbon ring system in which one or more of the atoms in the ring system is an element other than carbon, chosen from nitrogen (and N-oxides), oxygen and sulphur. Heterocyclo means a 4 to 10 membered saturated or partially saturated monocyclic or multicyclic hydrocarbon ring system in which one or more of the atoms in the ring system is an element other than carbon, chosen from amongst nitrogen, oxygen or sulphur. Heteroarylalkyl means a heteroaryl-alkyl-group and heterocycloalkyl means a heterocyclo-alkyl-group. Alkylcarbonyl means an alkyl-CO-group in which the alkyl group is as previously described. Arylcarbonyl means an aryl-CO-group in which the aryl group is as previously described. Heteroarylcarbonyl means a heteroaryl-CO-group and heterocyclocarbonyl means a heterocyclo-CO-group. Arylsulphonyl means an aryl-$SO_2$-group in which the aryl group is as previously described. Heteroarylsulphonyl means a heteroaryl-$SO_2$-group and heterocyclosulphonyl means a heterocyclo-$SO_2$-group. Alkoxycarbonyl means an alkoxy-CO-group in which the alkoxy group is as previously described. Alkylsulphonyl means an alkyl-$SO_2$-group in which the alkyl group is as previously described. Heterocyclic ring means a 4 to 10 membered monocyclic or multicyclic ring system (which may saturated or partially unsaturated) wherein one or more of the atoms in the ring system is an element other than carbon chosen from amongst nitrogen, oxygen or sulphur atoms. Halogen means fluorine, chlorine, bromine or iodine.

The invention further provides a process for the preparation of a compound of formula (i), in which $R_1$–$R_{25}$, p, X, Y and Z are as defined above. It will be appreciated that functional groups such as amino, hydroxyl, carbonyl or carboxyl groups present in the various compounds described below, and which it is desired to retain, may need to be in protected forms before any reaction is initiated. In such instances, removal of the protecting group may be the final step in a particular reaction. Suitable protecting groups for such functionality will be apparent to those skilled in the art. For specific details, see Protective Groups in Organic Synthesis, Wiley Interscience, T W Greene.

Thus the process for preparing compounds of formula (i) in which $R_2$ contains an —OH comprises deprotecting (for example by hydrogenolysis or hydrolysis) a compound of formula (i) in which $R_2$ contains an appropriate —OP wherein P represents a suitable protecting group (eg benzyl or acetyl). The process for preparing compounds of formula (i) in which $R_2$ contains a carbonyl group may comprise of deprotecting (for example by acidic hydrolysis) a compound of formula (i) in which $R_2$ contains an appropriate $CP_2$ moiety where P represents a suitable protecting group (eg alkoxy).

A process for the preparation of a compound of formula (i) in which Z is CO comprises reaction of an appropriate carboxylic acid of formula (ii) with a suitable amine of formula (iii)

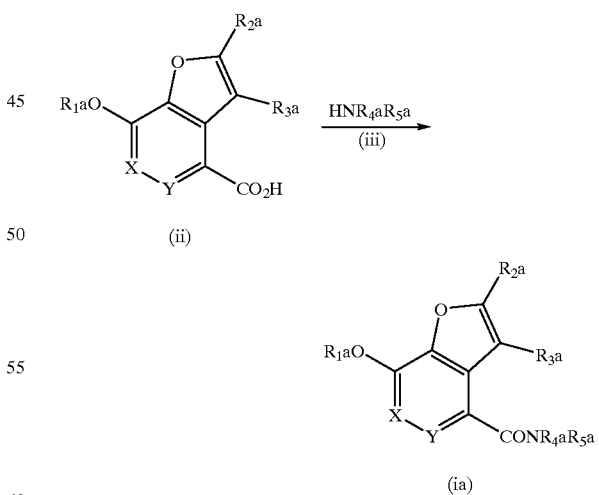

(ii)

(ia)

wherein $R_1a$ represents $R_1$ as defined in relation to formula (i) or a group convertable to $R_1$ and $R_2a$–$R_5a$ similarly represent $R_2$–$R_5$ or groups convertable to $R_2$–$R_5$ respectively and thereafter, if required, converting any group $R_1a$ to $R_1$ and/or $R_2a$ to $R_2$ and/or $R_3a$ to $R_3$ and/or $R_4a$ to $R_4$ and/or $R_5a$ to $R_5$. The reaction of a carboxylic acid of formula (ii) with an amine of formula (iii) may be carried out under any suitable conditions known to those skilled in the art. Favourably the carboxylic acid is converted into an acid chloride, mixed anhydride, p-nitrophenyl ester or other activated intermediate prior to reaction with an amine of formula (iii). Favourably the reaction with the amine of formula (iii) is carried out in the presence of a suitable base, for example an amine such as triethylamine, preferably in an appropriate solvent such as dichloromethane. In some cases a stronger base, such as sodium hydride, and a polar solvent such as dimethylformamide, will be required.

Carboxylic acids of formula (ii) are either previously described compounds or are prepared using standard procedures known to those skilled in the art. For example a carboxylic acid of formula (ii) is conveniently prepared from an appropriate compound of formula (v). Conversion of a compound of formula (v) to a carboxylic acid of formula (ii) can be carried out using any standard procedures known to those skilled in the art. For example, a compound of formula (v) can be formylated to provide an aldehyde of formula (iv), which can then be oxidised to provide the corresponding acid of formula (ii). Alternatively, a compound of formula (v) can be brominated to provide a bromide of formula (vi), which can then be converted into a carboxylic acid of formula (ii), for example by organometal catalysed carboxylation or by generation of a Grignard reagent followed by quenching with carbon dioxide.

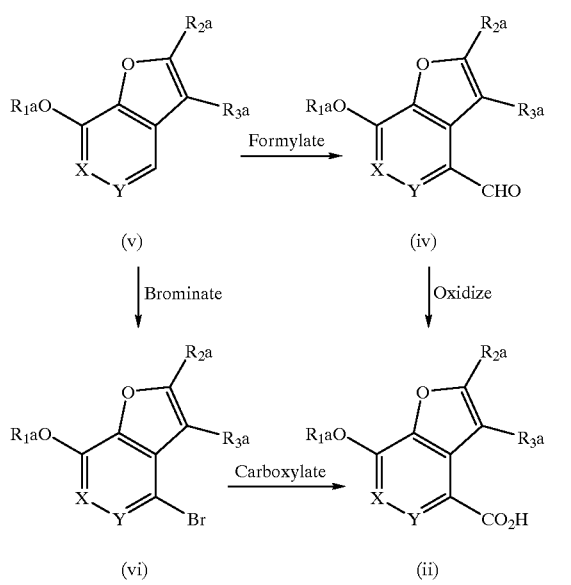

Compounds of formula (v) may be prepared by any standard procedure known to those skilled in the art, for example by treatment of a compound of formula (viii) with a strong base (such as butyllithium), and, if necessary, conversion to a Grignard or other organometallic species, followed by reaction with an agent $R_2aW$ where W is a suitable leaving group such as a halogen, or an agent G, where G contains for example, a reactive carbonyl moiety or a nitrile, and after reaction constitutes the group $R_2a$. A compound of formula (viii), when X is N and Y is CH or N, may be prepared by any standard procedure known to those skilled in the art, for example by the reaction of a compound of formula (vii) where Q is a suitable leaving group such as a halogen with an agent such as $R_1aOM$ where M is a metal counter ion such as sodium. A compound of formula (vii) may be prepared by any standard procedure known to those skilled in the art, for example when X is N, by the procedures described in *J. Heterocyclic Chem.*, 1982, 19, 1207–1209 or *Bull. Soc. Chim. Fr.*, 1968, 4959–4967. A compound of formula (viii), when X is CH and Y is N, may be prepared by any standard procedure known to those skilled in the art, for example by the hydrolysis of a compound of formula (ix) in which K is, for example, a substituent such as acetoxy to a compound of formula (ix) in which K is, for example, a hydroxyl group and subsequent treatment with an alkylating agent $R_1aW$, where W is a suitable leaving group such as a halogen, in the presence of a suitable base such as sodium hydride in an appropriate solvent such as THF. A compound of formula (ix) when X is CH may be prepared by any standard procedure known to those skilled in the art, for example by the procedures described in *J. Heterocyclic Chem.*, 1996, 33, 647–654

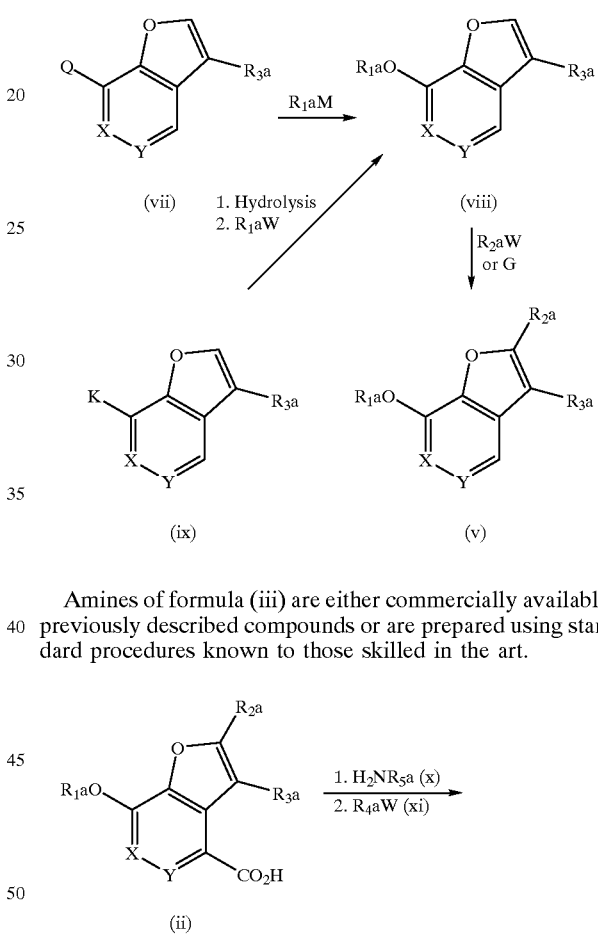

Amines of formula (iii) are either commercially available, previously described compounds or are prepared using standard procedures known to those skilled in the art.

compound of formula (ia) may also be prepared by reaction of a carboxylic acid of formula (ii) with an amine of formula (x) to provide a compound of formula (ia) in which $R_4a$ is H, followed by reaction with an appropriate alkylating agent of formula (xi), wherein $R_1a$–$R_5a$ are as defined earlier and W represents a suitable leaving group such as a halogen. The reaction of a carboxylic acid of formula (ii) with an amine of formula (x) may be carried out under any suitable conditions known to those skilled in the art. Favourably the carboxylic acid is converted into an acid chloride, mixed anhydride, p-nitrophenyl ester or other activated intermediate prior to reaction with an amine of formula (x). Favourably the reaction with the amine of formula (x) is carried out in the presence of a suitable base, for example an amine such as triethylamine, preferably in an appropriate solvent such as dichloromethane. In some cases a stronger base such as sodium hydride, and a polar solvent such as dimethylformamide, may be required.

Amines of formula (x) are either commercially available, previously described compounds or are prepared using standard procedures known to those skilled in the art. The reaction of a compound of formula (ia) in which $R_4a$ is H with an alkylating agent of formula (xi) may be carried out under any suitable conditions known to those skilled in the art. Favourably the reaction is carried out using an appropriate base, such as sodium hydride, preferably in an appropriate solvent such as dimethylformamide. Alkylating agents of formula (xi) are either commercially available or are prepared using standard procedures known to those skilled in the art.

Some compounds of formula (i) may be prepared from other compounds of formula (i). For example, compounds in which $R_2$ contains an oxime may be prepared from compounds in which $R_2$ contains a carbonyl group. This transformation may be carried out using any appropriate standard conditions known to those skilled in the art. For example the transformation may be achieved in one step by reaction of a compound of formula (i) with an appropriate hydroxylamine under suitable conditions. Suitable conditions include the use of a base, such as pyridine in a dry solvent such as toluene at an appropriate temperature such as the reflux temperature of the solvent. The use of a Dean and Stark apparatus to remove the water generated may also be considered appropriate. Alternatively, the transformation may involve two steps, ie reaction of the ketone with hydroxylamine followed by alkylation of the resulting oxime with an approriate alkylating agent. The reaction with hydroxylamine may involve the use of a base, such as pyridine in a dry solvent such as toluene at an appropriate temperature such as the reflux temperature of the solvent. The use of a Dean and Stark apparatus to remove the water generated may also be considered appropriate. The alkylation can be conducted under any suitable conditions known to those skilled in art. Suitable conditions include the use of an appropriate base such as sodium hydride in an appropriate anhydrous solvent such as DMF. Some compounds of formula (i) in which $R_2$ contains an oxime can be prepared by further modification of the oxime substituent after alkylation if the alkylating agent contains appropriate functionality. For example, if $R_2$ contains an amide, this can be prepared by reaction of an appropriate carboxylic acid with a suitable amine under standard conditions known to those skilled in the art. Standard conditions include the use of a suitable coupling agent such as 1-(3-dimethylaminopropyl)-3-ethylcarbodiimide hydrochloride in an appropriate solvent such as dichloromethane in the presence of a suitable base such as triethylamine. An appropriate carboxylic acid may be conveniently prepared by hydrolysis of an appropriate ester. An appropriate ester may be obtained if an alkylating agent incorporating an ester is used. An example of such an alkylating agent is t-butyl chloroacetate.

Compounds of formula (i) in which $R_2$ contains a carbonyl group may be prepared from compounds of formula (i) in which $R_2$ contains a hydroxyl group by oxidation using any standard conditions known to those skilled in the art. Suitable conditions include the use of DMSO and oxalyl chloride in the presence of a suitable base such as triethylamine in an appropriate anhydrous solvent such as dichloromethane.

Compounds of formula (i) in which $R_2$ contains a carbonyl group may be reduced using standard conditions known to those skilled in the art (for example with sodium borohydride in an appropriate solvent) to provide compounds in which $R_2$ contains an alcohol group. The alcohol thus obtained may be alkylated using any suitable conditions known to those skilled in art. Suitable conditions include the use of an appropriate base such as sodium hydride in an appropriate anhydrous solvent such as DMF.

Compounds of formula (i) in which $R_2$ contains an amine group may be prepared from compounds of formula (i) in which $R_2$ contains a carbonyl group using any standard conditions known to those skilled in the art, such as reductive amination. Suitable conditions include the use of a reducing agent such as sodium triacetoxyborohydride in an appropriate solvent such as dichloroethane in the prescence of a drying agent such as activated molecular sieves. The addition of acetic acid may also be beneficial.

By way of further example, compounds of formula (i) may also be prepared by a Wittig or similar reaction, followed by reduction of the double bond, using conditions known to those skilled in the art, on a compound of formula (ia) where $R_2a$ contains either an aldehyde or ketone moiety.

Compounds of formula (i) in which Z is CS may be prepared from compounds of formula (i) in which Z is CO using any appropriate conditions known to those skilled in the art, for example by using Lawesson's reagent.

Compounds of formula (i) which contain an N-oxide may be prepared using any appropriate conditions known to those skilled in the art, for example by treating a compound of formula (i) containing a heteroaryl N-atom with peracetic acid in acetic acid in an appropriate solvent such as chloroform.

It will be appreciated by those skilled in the art that in some cases it may more appropriate to carry out the above mentioned transformations of a carbonyl group on compounds of formula (ii), (vi) or (v) rather than compounds of formula (i).

It will be appreciated that where a particular stereoisomer of formula (i) is required, this may be obtained by conventional resolution techniques such as high performance liquid chromatography or the synthetic processes herein described may be performed using the appropriate homochiral starting material.

The invention includes the prevention and treatment of TNF mediated disease or disease states, by which is meant any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biological responses and binds to the same cellular receptor, both TNF-α and TNF-β are assumed to be inhibited by compounds of the present invention and thus are herein referred to collectively as "TNF" unless specifically delineated otherwise.

PDE IV inhibitors are useful in the treatment of a variety of allergic and inflanrnatory diseases, including: asthma, chronic obstructive pulmonary disease, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

Inhibitors of PDE IV are useful for the treatment of viral diseases.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (i) are preferably in pharmaceutically-acceptable form. By pharmaceutically-acceptable form is meant, inter alia, a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%. When used herein the term "pharmaceutically-acceptable" encompasses materials suitable for both human and veterinary use.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose. Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose, or pharmaceutically-acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 μm, such as from 0.1 to 50 μm, preferably less than 10 μm, for example from 1 to 10 μm, 1 to 5 μm or from 2 to 5 μm. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions, the compound can be dissolved in water for injection and filter-sterilised before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and U.S. Pharmacopoeias.

Suitably, the compound of formula (i), or if appropriate a pharmaceutically-acceptable salt thereof, will comprise from about 0.5 to 20% by weight of the formulation, preferably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

ASSAY METHODS

The assays used to confirm the phosphodiesterase IV inhibitory activity of compounds of formula (I) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be usefull in treating phosphodiesterase IV-related disease states in those assays.

The ability of compounds of formula (i) to inhibit TNF production in human peripheral blood mononuclear cells (PMBC's) is measured as follows. PMBC's are prepared from freshly taken blood or "Buffy coats" by standard procedures. Cells are plated out in RPMI 1640+1% foetal calf serum in the presence and absence of inhibitors. LPS (100 ng/ml) is added and cultures are incubated for 22 h at 37° C. in an atmosphere of 95% air/5% $CO_2$. Supernatants are tested for TNFα by ELISA using commercially available kits.

Abbreviations

LPS Lipopolysaccharide (endotoxin)

ELISA Enzyme linked immunosorbent assay

Activity in a guinea pig lung model is measured using the procedures described by Mauser et al, Am. Rev. Respir. Dis. 148 1623 (1993) and Am. J. Respir. Crit. Care Med. 152 467 (1995).

The pharmacokinetic profile of the compounds of the invention is determined in rats cannulated in the right carotid artery for blood collection. For iv dosing, the compound is prepared in a suitable formulation, for example 10% v/v DMSO, 50% v/v PEG 400 in water, and dosing is carried out by cannulation of the left jugular vein. Samples are collected at 5 min, 0.5, 1, 2, 4, 6 and 8 hours post-dosing. For oral dosing, the compound is prepared in a suitable formulation such as 0.4% w/v methylcellulose in water. Samples are collected at 0.5, 1, 2, 4, 6 and 8 hours post-dosing. In some cases, samples are also collected at 12 hours post-dosing. Plasma is obtained by centrifugation of the each blood sample and drug concentration is then determined using standard methods, such as liquid chromatography-mass spectrometry following protein precipitation.

The following Examples illustrate the invention.

INTERMEDIATE 1

6-H-Furo[2,3-c]pyridin-7-one

A solution of furan-3-acrylic acid (6.2 g) in acetone (62 ml) was stirred at −10° C. (ice/methanol) under an atmosphere of dry nitrogen. Triethylamine (5.9 g) was added in one portion followed by dropwise addition of isobutyl chloroformate (5.7 g), maintaining the temperature below 0° C. After stirring for 30 minutes a solution of sodium azide (4.4 g) in water (20 ml) was added dropwise, again maintaining the temperature below 0° C. and the resulting mixture stirred at room temperature for 3 h. The mixture was then poured onto ice (300 ml) and the resulting solid collected by filtration, washed with water and dried in vacuo to give the acyl azide which was used without further purification.

A mixture of diphenylmethane (26 ml) and tributylamine (7 ml) was stirred at 235° C. The acyl azide (6.6 g) prepared above was added portionwise as a solid and the resulting mixture stirred at 235° C. for 15 minutes before being cooled to room temperature. Purification by flash column chromatography on silica eluting with 50% hexane in ethyl acetate to 2% methanol in ethyl acetate followed by trituration with diethyl ether gave the title compound (1.7 g) as a brown solid.
TLC $R_f$ 0.26 (ethyl acetate)

INTERMEDIATE 2

7-Chlorofuro[2,3-c]pyridine

A solution of 6-H-furo[2,3-c]pyridin-7-one (1.0 g) in phosphorous oxychloride (10 ml) was stirred at 110° C. for 30 minutes under dry nitrogen. The mixture was cooled, poured onto ice/water (50 ml) and basified to pH10 with 2N sodium hydroxide solution. The mixture was extracted with ether (3×50 ml), the combined extracts dried over sodium sulfate and filtered. Removal of the solvent in vacuo gave the title compound (1.0 g) as a white solid.
TLC $R_f$ 0.75 (ethyl acetate)

INTERMEDIATE 3

7-Methoxyfuro[2,3-c]pyridine

A solution of 7-chlorofuro[2,3-c]pyridine (1.1 g) was stirred at room temperature under dry nitrogen in 1,4-dioxane (40 ml). Sodium methoxide (1.2 g) was added and the resulting mixture heated at reflux overnight. The mixture was diluted with water (100 ml) then extracted with ethyl acetate (3×100 ml). The combined organic extracts were washed with brine (50 ml), dried over magnesium sulfate, filtered and the solvent removed in vacuo to give the title compound (0.96 g) as a brown oil.
TLC $R_f$ 0.68 (50% hexane in ethyl acetate)

INTERMEDIATE 4

1-(7-Methoxyfuro[2,3-c]pyridin-2-yl)ethanol

A solution of 7-methoxyfuro[2,3-c]pyridine (1.5 g) in dry tetrahydrofuran (50 ml) was stirred at −78° C. under dry nitrogen. n-Butyllithium (1.6N solution in hexanes, 6.9 ml) was added dropwise and the resulting solution stirred at −78° C. for 60 minutes. Acetaldehyde (5.7 ml) was added and stirring continued at −78° C. for 90 minutes before warming to room temperature. The mixture was diluted with water (100 ml) and extracted with ethyl acetate (3×100 ml). The combined organic extracts were dried over magnesium sulfate, filtered and the solvent removed in vacuo. Purification by column chromatography on silica eluting with 50% hexane in ethyl acetate gave the title compound (1.8 g) as a brown oil.
TLC $R_f$ 0.50 (50% hexane in ethyl acetate)
The following compounds were prepared in a similar manner.

INTERMDIATE 5

2-Ethyl-7-methoxyfuro[2,3-c]pyridine

Starting from 7-methoxyfuro[2,3-c]pyridine (4.5 g) and ethyl iodide (4.0 ml). Purification by column chromatography on silica eluting with 70% hexane in ethyl acetate gave the title compound (30 g) as a colourless oil.
TLC $R_f$ 0.66 (70% hexane in ethyl acetate)

INTERMEDIATE 6

4-(7-Methoxyfuro[2,3-c]pyridin-2-yl)tetrahydopyran-4-ol

Starting from 7-methoxyfuro[2,3-c]pyridine (1.5 g) and tetrahydro-4H-pyran one (1.0 ml). Purification by column chromatography on silica eluting with 50% hexane in ethyl acetate gave the title compound (2.5 g) as a colourless oil.
TLC $R_f$ 0.37 (50% hexane in ethyl acetate)

INTERMEDIATE 7

(7-Methoxyfuro[2,3-c]pyridin-2-yl)methanol

Starting from 7-methoxyfuro[2,3-c]pyridine (2.06 g) and formaldehyde (27 ml). Purification by column chromatography on silica eluting with 50% hexane in ethyl acetate gave the title compound (1.4 g) as a white solid.
TLC $R_f$ 0.45 (50% hexane in ethyl acetate)

INTERMEDIATE 8

2-Bromo-7-methoxyfuro[2,3-c]pyridine

Starting from 7-methoxyfuro[2,3-c]pyridine (1.0 g) and bromine (0.34 ml). Purification by column chromatography on silica eluting with 2:1 heptane:ethyl acetate gave the tite compound (1.2 g) as a white solid.
TLC $R_f$ 0.56 (3:1 ethyl acetate:hexane)

INTERMEDIATE 9

3-(7-Methoxyfuro[2,3-c]pyridin-2-yl)tetrahydrofuran-3-ol

Starting from 7-methoxyfuro[2,3-c]pyridine (2.5 g) and dihydrofuran-3-one (1.7 g). Purification by column chromatography on silica eluting with 50% ethyl acetate in heptane afforded the title compound as a brown oil (2 g).
TLC $R_f$ 0.33 (50% ethyl acetate in hexane)

INTERMEDIATE 10

4-Hydroxy-4-(7-methoxyfuro[2,3-c]pyridin-2-yl)piperidine-1-carboxylic acid tert-butyl ester Starting from 7-methoxfuro[2,3-c]pyridine (2 g) and N-tert-butyloxycarbonyl-4-piperidinone (2.44 g). Purification by column chromatography on silica eluting with 50% ethyl acetate in hexane gave the title compound (3.07 g) as a white solid.
TLC $R_f$ 0.30 (50% ethyl acetate in hexane)

INTERMEDIATE 11

2-Acetyl-7-methoxyfuro[2,3-c]pyridine

A solution of oxalyl chloride (0.97 ml) in dry dichloromethane (10 ml) was stirred at −55° C. under an atmosphere of dry nitrogen. A solution of dimethyl sulfoxide (1.7 ml) in dry dichloromethane (5 ml) was added dropwise and stirring continued for 5 minutes at −55° C. 1-(7-Methoxyfuro[2,3-c]pyridin-2-yl)ethanol (1.9 g) in dimethyl sulfoxide (15 ml) was added dropwise and stirring continued for a further 15 minutes. Triethylamine (6.9 ml) was added and the mixture stirred for a further 5 minutes at −55° C. before warming to room temperature. The mixture was diluted with water (100 ml) and extracted with dichloromethane (3×100 ml). The combined organic extracts were dried over magnesium sulfate, filtered and the solvent removed in vacuo. Purification by column chromatography on silica eluting with 50% hexane in ethyl acetate gave the title compound (1.2 g) as a pale yellow solid.
TLC $R_f$ 0.66 (50% hexane in ethyl acetate)

INTERMEDIATE 12

7-Methoxy-2-(tetrahydropyran-4-yl)furo[2,3-c]pyridine

A solution of 4-(7-methoxyfuro[2,3-c]pyridin-2-yl)tetrahydopyran-4-ol (2.5 g) in dry dichloromethane (50 ml) was stirred at 0° C. under an atmosphere of dry nitrogen. Triethylamine (5.6 ml) was added followed by methanesulfonyl chloride (2.3 ml). The mixture was stirred overnight at room temperature. The solvent was removed in vacuo. Purification by column chromatography on silica eluting with 50% hexane in ethyl acetate gave 2-(3,6-dihydro-2H-pyran-4-yl)-7-methoxyfuro[2,3-c]pyridine (2.5 g) as a colourless oil.

A solution of the alkene (1.0 g) in ethanol (50 ml) was treated with Raney Nickel and hydrogenated at atmospheric pressure for 4 hours. The mixture was filtered through Celite and the solvent was removed in vacuo to give the title compound (1.0 g) as a creamy oil.
TLC $R_f$ 0.53 (66% hexane in ethyl acetate)

The following compound was prepared in a similar manner.

INTERMEDIATE 13

7-Methoxy-2-(tetrahydrofuran-3-yl)furo[2,3-c]pyridine

Starting from 3-(7-methoxyfuro[2,3-c]pyridin-2-yl)tetrahydrofuran-3-ol (2.02 g). Purification by column chromatography on silica eluting with 33% ethyl acetate in heptane afforded the title compound as a yellow gum (0.9 g).
TLC $R_f$ 0.38 (33% ethyl acetate in hexane)

INTERMEDIATE 14

7-Methoxy-2-methoxymethylfuro[2,3-c]pyridine

Sodium hydride (780 mg) was added to a solution of (7-methoxyfuro[2,3-c]pyridin-2-yl)methanol (1.4 g) in tetrahydrofuran at room temperature under nitrogen. The mixture was stirred for 5 minutes before addition of iodomethane (1.5 ml) took place. Stirring was continued for a further 3 hours. The reaction was quenched with water (2 ml) and the solvent removed in vacuo. The residue was partitioned between water (75 ml) and ethyl acetate (75 ml), extracted with ethyl acetate (70 ml) and the combined extacts were dried with magnesium sulphate and purified by column chromatography eluting with 50% ethyl acetate in hexane.
TLC $R_f$ 0.65 (50% ethyl acetate in hexane)

INTERMEDIATE 15

4-methoxy-4-(7-methoxyfuro[2,3-c]pyridin-2-yl)piperidine-1-carboxylic acid tert-butyl ester A solution of 4-methoxy-4-(7-methoxyfuro[2,3-c]pyridin-2-yl)piperidine carboxylic acid tert-butyl alcohol (8.59 g) in dry N,N-dimethylformamide (100 ml) was stirred at room temperature under an atmosphere of dry nitrogen. Sodium hydride (60% in oil, 1.18 g) was added portionwise and stirring continued for 30 minutes. Iodomethane (3.07 ml) was added and stirring continued for 80 minutes. The mixture was diluted with ethyl acetate (300 ml) and washed with water (4×100 ml) and brine (1×100 ml). The organic extract was dried over magnesium sulphate, filtered and the solvent removed in vacuo to give the title compound (10.19 g) as a pale yellow liquid.
TLC $R_f$ 0.425 (50% ethyl acetate in hexane)

INTERMEDIATE 16

7-Methoxy-2-pyridin-3-yl-furo[2,3-c]pyridine

2-Bromo-7-methoxyfuro[2,3-c]pyridine (0.6 g), diethyl (3-pyridyl)borane (0.387 g), tetrakis(triphenylphosphine)palladium(O) (0.157 g), potassium hydroxide (0.442 g) and tetrabutyl ammonium iodide (0.486 g) were combined in dry tetrahydrofuran (25 ml) under dry nitrogen. The mixture was heated to reflux for 1 hour. The solvent was removed in vacuo, and the residue partitioned between dichloromethane (20 ml) and water (20 ml). The aqueous layer was extracted with dichloromethane (20 ml). The combined organics were washed with water (24×40 ml), dried over magnesium sulfate, filtered and the solvent removed in vacuo. Purification by column chromatography on silica eluting with 2:1 heptane:ethyl acetate gave the title compound (0.30 g) as a white solid.
TLC $R_f$ 0.18 (2:1 ethyl acetate:hexane)

INTERMEDIATE 17

2-Acetyl-4-bromo-7-methoxyfuro[2,3-c]pyridine

A solution of 2-acetyl-7-methoxyfuro[2,3-c]pyridine (1.1 g) in acetonitrile (50 ml) was stirred at room temperature. N-Bromosuccinimide (1.0 g) was added and stirring continued overnight. The reaction was quenched by the addition of water (50 ml) and extracted with dichloromethane (3×50 ml). The combined organic extracts were washed with water (50 ml), dried over magnesium sulfate, filtered and the solvent removed in vacuo. Purification by column chromatography on silica eluting with 33% ethyl acetate in hexane gave the title compound (1.4 g) as a white solid.
TLC $R_f$ 0.71 (33% ethyl acetate in hexane)

The following compounds were prepared in a similar manner.

INTERMEDIATE 18

2-Ethyl-4-bromo-7-methoxyfuro[2,3-c]pyridine

Starting from 2-ethyl-7-methoxyfuro[2,3-c]pyridine (3.0 g). Purification by column chromatography on silica eluting with 80% hexane in ethyl acetate gave the title compound (3.5 g) as a white solid.
TLC $R_f$ 0.80 (80% hexane in ethyl acetate)

INTERMEDIATE 19

4-bromo-7-methoxy-2-(tetrahydropyran-4-yl)furo[2,3-c]pyridine

Starting from 7-methoxy-2-(tetrahydropyran-4-yl)furo[2,3-c]pyridine (1.0 g). Purification by column chromatography on silica eluting with 66% hexane in ethyl acetate gave the title compound (0.83 g) as a white solid.
TLC $R_f$ 0.53 (66% hexane in ethyl acetate)

INTERMEDIATE 20

4-Bromo-7-methoxy-2-methoxymethylfuro[2,3-c]pyridine

Starting from 7-Methoxy-2-methoxymethylfuro[2,3-c]pyridine (200 mg). Purification by column chromatography on silica eluting with 20% ethyl acetate in hexane gave the title compound (182 mg) as a white solid.
TLC $R_f$ 0.65 (25% ethyl acetate in hexane)

INTERMEDIATE 21

4-Bromo-7-methoxy-2-pyridin-3-yl-furo[2,3-c] pyridine

Starting from 7-methoxy-2-pyridin-3-yl-furo[2,3-c]pyridine (1.3 g). Purification by column chromatography on silica eluting with 50% ethyl acetate in hexane gave the title compound as a cream solid (1.38 g).
TLC $R_f$ 0.28 (1:1 hexane:ethyl acetate)

INTERMEDIATE 22

4-Bromo-7-methoxy-2-(tetrahydrofuran-3-yl)furo[2,3-c]pyridine

Starting from 7-methoxy-2-(tetrahydrofuran-3-yl)furo[2,3-c]pyridine (0.9 g). After extraction into dichloromethane (2×70 ml) the title compound was given as an orange gum (1.14 g).
TLC $R_f$ 0.54 (33% ethyl acetate in heptane)

INTERMEDIATE 23

4-(4-Bromo-7-methoxyfuro[2,3-c]pyridin-2-yl)-4-methoxypiperidine-1-carboxylic acid tert-butyl ester Starting from 4-methoxy-4-(7-methoxyfuro[2,3-c]pyridin-2-yl)piperidine-1-carboxylic acid tert-butyl ester (8.93 g). Purification by column chromatography on silica eluting with 40% ethyl acetate in hexane gave the title compound (6.13 g) as a white solid.
TLC $R_f$ 0.60 (50% ethyl acetate in hexane)

INTERMEDIATE 24

4-Bromo-2-(1,1-dimethoxyethyl)-7-methoxyfuro[2,3-c]pyridine

A solution of 2-acetyl-4-bromo-7-methoxyfuro[2,3-c]pyridine (1.4 g), trimethylorthoformate (1.1 g) and p-toluenesulfonic acid monohydrate (1.2 g) in dry methanol (50 ml) was heated at reflux for 3 h. The mixture was cooled and the methanol removed in vacuo. The residue was taken up in ethyl acetate (100 ml), washed with saturated sodium bicarbonate solution (50 ml) and brine (50 ml), dried over magnesium sulfate, filtered and the solvent removed in vacuo. Purification by column chromatography on silica eluting with 33% ethyl acetate in hexane gave the title compound (contaminated with 15% 2-acetyl-4-bromo-7-methoxyfuro[2,3-c]pyridine) as a white solid (1.0 g).
TLC $R_f$ 0.73 (33% ethyl acetate in hexane)

INTERMEDIATE 25

4-Bromo-7-methoxy-2-(4-methoxypiperidin-4-yl)furo[2,3-c]pridine 4-(4-Bromo-7-methoxyfuro[2,3-c]pyridin-2-yl)-4-methoxypiperidine-1-carboxylic acid tert-butyl ester (1.5 g), dichloromethane (50 ml) and trifluoroacetic acid (5 ml ) were combined and stirred at room temperature for 3 hours. The reaction mixture was then diluted with 1N sodium hydroxide solution (100 ml) and extracted with dichloromethane (3×50 ml). The combined extracts were then dried over magnesium sulphate and evaporated in vacuo to give the title compound (1.2 g) as a pale yellow oil.
TLC $R_f$ 0.075 (50% ethyl acetate in hexane)

INTERMEDIATE 26

4-Bromo-7-methoxy-2-(4-methoxy-1-methylpiperidin-4-yl)furo[2,3-c]pyridine

4-Bromo-7-methoxy-2-(4-methoxypiperidin-4-yl)furo[2,3-c]pyridine (1.2 g), formic acid (0.76 ml) and formaldehyde (37% w/w aqueous solution) (0.66 g) were combined and heated to 95° C. for 24 hours. The reaction mixture was then diluted with 2N sodium hydroxide solution (100 ml) and extracted with ethyl acetate (3×50 ml). The combined extracts were then dried over magnesium sulphate and evaporated in vacuo to give the title compound (0.96 g) as a pale yellow oil.
M.S. [M+H] observed

INTERMEDIATE 27

4-Bromo-2-ethyl-6H-furo[2,3-c]pyridin-7-one

To a stirred solution of sodium hydride (50 mg) (60% suspension in mineral oil) in dry N,N-dimethylformamide (3 ml) under an atmosphere of dry nitrogen at room temperature was added dropwise a solution of ethanethiol (0.09 ml) in N,N-dimethylformamide (3 ml). After stirring for 10 mins a solution of 2-ethyl-4-bromo-7-methoxyfuro[2,3-c]pyridine (200 mg) in N,N-dimethylformamide (5 ml) was added dropwise and the reaction mixture heated at 150° C. for 60 mins. Water (5 ml) was added and the solvent removed in vacuo. The residue was dissolved in ethyl acetate (100 ml), washed with ammonium chloride solution (25 ml), water (25 ml) and brine (25 ml), dried over magnesium sulphate, filtered and the solvent removed in vacuo. Purification by column chromatography on silica eluting with ethyl actate afforded the title compound as a white solid (169 mg).
TLC $R_f$ 0.39 (ethyl acetate)

INTERMEDIATE 28

4-Bromo-7-difluoromethoxy-2-ethylfuro[2,3-c] pyridine

To a solution of 4-bromo-2-ethyl-6H-furo[2,3-c]pyridin-7-one (500 mg) in 1,4-dioxane (30 ml) heated to 100° C. was added dropwise a solution of sodium hydroxide (250 mg) in water (2 ml). Chlorodifluoromethane was bubbled through the reaction mixture for 15 mins after which it was allowed to cool to room temperature and stirred for 18 hours. The solvent was removed in vacuo and the residue dissolved in water (10 ml), acidified to pH3 using 1M hydrochloric acid, extracted with ethyl acetate (150 ml) and washed with brine (20 ml). The organic layer was separated, dried over magnesium sulphate, filtered and the solvent removed in vacuo. Purification by column chromatography on silica eluting with 10% ethyl acetate in hexane afforded the title compound as a white solid (240 mg).
TLC $R_f$ 0.60 (20% ethyl acetate in hexane)

INTERMEDIATE 29

2-(1,1-Dimethoxyethyl)-7-methoxyfuro[2,3-c] pyridine-4-carboxylic acid

4-Bromo-2-(1,1-dimethoxyethyl)-7-methoxyfuro[2,3-c]pyridine (1.0 g), palladium acetate (71 mg), bis-diphenylphosphinopropane (0.26 g), triethylamine (4.4 ml), tetrahydrofuran (60 ml) and water (30 ml) were combined in a Parr pressure reactor. The vessel was purged with carbon monoxide 3 times before being charged with carbon monoxide at 965 kPa (140 psi). The vessel was then heated at 90° C. for 3 days before cooling and release of the pressure. The reaction mixture was concentrated in vacuo and the residue taken up in 1N sodium hydroxide solution (100 ml). The mixture was washed with ethyl acetate (2×100 ml) then acidified to pH4 with glacial acetic acid. The resulting mixture was extracted with dichloromethane (2×100 ml), the combined organic extracts dried over magnesium sulfate, filtered and the solvent removed in vacuo. Co-evaporation from toluene to remove excess acetic acid gave the title compound (contaminated with 30% 2-acetyl-7-methoxyfuro [2,3-c]pyridine-4-carboxylic acid) as a white solid (0.66 g). TLC $R_f$ 0.52 (50% hexane in ethyl acetate)

The following compounds were prepared in a similar manner.

INTERMEDIATE 30

2-Ethyl-7-methoxyfuro[2,3-c]pyridine-4-carboxylic acid

Starting from 2-ethyl-4-bromo-7-methoxyfuro[2,3-c] pyridine (3.5 g). The title compound (2.6 g) was obtained as a white solid.
TLC $R_f$ 0.61 (50% hexane in ethyl acetate)

INTERMEDIATE 31

7-Methoxy-2-(tetrahydropyran-4-yl)furo[2,3-c] pyridine 4-carboxylic acid

Starting from 4-bromo-7-methoxy-2-(tetrahydropyran-4-yl)furo[2,3-c]pyridine (1.4 g). The title compound (0.9 g) was obtained as a yellow solid.
TLC $R_f$ 0.81 (ethyl acetate)

INTERMEDIATE 32

7-Methoxy-2-methoxymethylfuro[2,3-c]pyridine-4-carboxylic acid

Starting from 4-bromo-7-methoxy-2-methoxymethylfuro [2,3-c]pyridine (1.44 g) the title compound (900 mg) was obtained as a white solid.
TLC $R_f$ 0.19 (50% ethyl acetate in hexane)

INTERMEDIATE 33

7-Methoxy-2-pyridin-3-yl-furo[2,3-c]pyridine-4-carboxylic acid

Starting from 4-bromo-7-methoxy-2-pyridin-3-yl-furo[2,3-c]pyridine (1.38 g). The title compound (0.74 g) was obtained as a brown solid.
TLC $R_f$ 0.21 (10% methanol in dichloromethane)

INTERMEDIATE 34

7-Methoxy-2-(tetrahydrofuran-3-yl)furo[2,3-c] pyridine-4-carboxylic acid

Starting from 4-bromo-7-methoxy-2-(tetrahydrofuran-3-yl)furo[2,3-c]pyridine (1.14 g). The title compound (0.62 g) was obtained as an orange gum.
TLC $R_f$ 0.49 (10% methanol in dichloromethane)

INTERMEDIATE 35

2-(1-tert-Butoxycarbonyl-4-methoxypiperidin-4-yl)-7-methoxyfuro[2,3-c]pyridine-4-carboxylic acid Starting from 4-(4-bromo-7-methoxyfuro[2,3-c]pyridin-2-yl)-4-methoxypiperidine-1-carboxylic acid tert-butyl ester (1 g). The title compound (0.63 g) was obtained as a white solid.
M.S. [M–H] observed

INTERMEDIATE 36

7-Methoxy-2-(4-methoxy-1-methylpiperidin-4-yl) furo[2,3-c]pyridine-4-carboxylic acid Starting from 4-bromo-7-methoxy-2-(4-methoxypiperidin-4-yl)furo[2,3-c]pyridine (0.96 g). The title compound was obtained as a white solid.
M.S. [M+H] observed

INTERMEDIATE 37

7-Difluoromethoxy-2-ethylfuro[2,3-c]pyridine-4-carboxylic acid

Starting from 4-bromo-7-difluoromethoxy-2-ethylfuro[2,3-c]pyridine (780 mg). The title compound was obtained as a pale yellow solid (360 mg).
TLC $R_f$ 0.11 (20% ethyl acetate in hexane)

INTERMEDIATES 38 and 39

2-(1,1-Dimethoxyethyl)-7-methoxyfuro[2,3-c] pyridine-4-carboxylic acid 4-nitrophenyl ester and 2-Acetyl-7-methoxyfuro[2,3-c]pyridine-4-carboxylic acid 4-nitrophenyl ester 2-(1,1-Dimethoxyethyl)-7-methoxyfuro[2,3-c]pyridine-4-carboxylic acid (0.66 g), p-nitrophenol (0.32 g), 1-(3-dimethylaminopropyl)-3-ethylcarbodiimide hydrochloride (0.49 g) and 4-dimethylaminopyridine (catalytic) in dry dichloromethane (40 ml) were stirred overnight at room temperature. The mixture was diluted with dichloromethane (50 ml), washed with water (100 ml), dried over magnesium sulfate, filtered and the solvent removed in vacuo. Purification by column chromatography on silica eluting with 33% hexane in ethyl acetate to 100% ethyl acetate gave 2-(1,1-dimethoxyethyl)-7-methoxyfuro[2,3-c]pyridine-4-carboxylic acid 4-nitrophenyl ester (0.51 g) and 2-acetyl-7-methoxyfuro[2,3-c]pyridine-4-carboxylic acid 4-nitrophenyl ester (0.20 g) as white solids.

2-(1,1-Dimethoxyethyl)-7-methoxyfuro[2,3-c]pyridine-4-carboxylic acid 4-nitrophenyl ester
TLC $R_f$ 0.50 (33% hexane in ethyl acetate)
2-Acetyl-7-methoxyfuro[2,3-c]pyridine-4-carboxylic acid 4-nitrophenyl ester
TLC $R_f$ 0.40 (33% hexane in ethyl acetate)

The following compounds were prepared in a similar manner.

INTERMEDIATE 40

2-Ethyl-7-methoxyfuro[2,3-c]pyridine-4-carboxylic acid 4-nitrophenyl ester

Starting from 2-ethyl-7-methoxyfuro[2,3-c]pyridine-4-carboxylic acid (1.6 g). Purification by column chromatography on silica eluting with 50% hexane in ethyl acetate followed by trituration with diethyl ether gave the title compound (1.6 g) as a white solid.
TLC $R_f$ 0.45 (66% hexane in ethyl acetate)

INTERMEDIATE 41

7-Methoxy-2-(tetrahydropyran-4-yl)furo[2,3-c] pyridine 4-carbooxylic acid 4-nitrophenyl ester Starting from 7-methoxy-2-(tetrahydropyran-4-yl)furo[2,3-c]pyridine 4-carboxylic acid (0.9 g). Purification by column chromatography on silica eluting with 50% hexane in ethyl acetate gave the title compound (0.7 g) as a yellow solid.
TLC R$_f$ 0.59 (50% hexane in ethyl acetate)

INTERMEDIATE 42

7-Methoxy-2-methoxymethylfuro[2,3-c]pyridine-4-carboxylic acid 4-nitrophenyl ester Starting from 7-methoxy-2-methoxymethylfuro[2,3-c]pyridine-4-carboxylic acid (450 mg). Purification by column chromatography on silica eluting with 30% ethyl acetate in hexane gave the title compound (400 mg) as a white solid.
TLC R$_f$ 0.76 (30% ethyl acetate in hexane)

INTERMEDIATE 43

7-Methoxy-2-pyridin-3-yl-furo[2,3-c]pyridine-4-carboxylic acid 4-nitrophenyl ester Starting from 7-methoxy-2-pyridin-3-yl-furo[2,3-c]pyridine-4-carboxylic acid (0.790 g). The title compound (0.822 g) was obtained as a pale yellow solid.
TLC R$_f$ 0.76 (10% methanol in dichloromethane)

INTERMEDIATE 44

7-Methoxy-2-(tetrahydrofuran-3-yl)furo[2,3-c]pyridine-4-carboxylic acid 4-nitrophenyl ester Starting from 7-methoxy-2-tetrahydrofuran-3-yl)furo[2,3-c]pyridine-4-carboxylic acid (0.62 g). After extraction into dichloromethane (50 ml) the title compound was obtained as a cream solid (0.62 g).
TLC R$_f$ 0.62 (2.5% methanol in dichloromethane)

INTERMEDIATE 45

2-(1-tert-Butoxycarbonyl-4-methoxypiperidin-4-yl)-7-methoxyfuro[2,3-c]pyridine-4-carboxylic acid 4-nitrophenyl ester Starting from 2-(1-tert-Butoxycarbonyl-4-methoxypiperidin-4-yl)-7-methoxyfuro[2,3-c]pyridine-4-carboxylic acid (0.63 g). No purification needed, to give the title compound (0.738 g) as a light yellow solid.
TLC R$_f$ 0.94 (5% methanol in dichloromethane)

INTERMEDIATE 46

7-Methoxy-2-(4-methoxy-1-methyl-piperidin-4-yl)furo[2,3-c]pyridine-4-carboxylic acid 4-nitrophenyl ester Starting from 7-methoxy-2-(4-methoxy-1-methyl-piperidin-4-yl)furo[2,3-c]pyridine-4-carboxylic acid (0.83 g). Purification by column chromatography on silica eluting with 10% methanol in dichloromethane gave the title compound (0.65 g) as a pale yellow solid.
TLC R$_f$ 0.475 (10% methanol in dichloromethane)

INTERMEDIATE 47

7-Difluoromethoxy-2-ethylfuro[2,3-c]pyridine-4-carboxylic acid 4-nitrophenyl ester Starting from 7-difluoromethoxy-2-ethylfuro[2,3-c]pyridine-4-carboxylic acid (350 mg). Purification by column chromatography on silica eluting with 20% ethyl acetate in hexane afforded the title compound as a white solid (420 mg).
TLC R$_f$ 0.45 (20% ethyl acetate in hexane)

INTERMEDIATE 48

2-(1,1-Dimethoxyethyl)-7-methoxyfuro[2,3-c]pyridine-4-carboxylic acid (3-methylpyridin-4-yl)amide A solution of 4-amino-3-methylpyridine (0.11 g) in dry N,N-dimethylformamide (20 ml) was stirred at 0° C. under an atmosphere of dry nitrogen. Sodium bis(trimethylsilyl)amide (1.0M solution in tetrahydrofuran, 1.0 ml) was added and stirring continued at 0° C. for 10 minutes. 2-(1,1-Dimethoxyethyl)-7-methoxyfuro[2,3-c]pyridine-4-carboxylic acid 4-nitrophenyl ester (0.20 g) was added and stirring continued at room temperature for 90 minutes. The solvent was then removed in vacuo, the residue taken up in water (100 ml) and extracted with ethyl acetate (3×100 ml). The combined organic extracts were washed with water (100 ml), then brine (50 ml), dried over magnesium sulfate, filtered and the solvent removed in vacuo. Purification by column chromatography on silica eluting with ethyl acetate gave the title compound (0.15 g) as a white solid.
TLC R$_f$ 0.31 (ethyl acetate)

EXAMPLE 1

2-Acetyl-7-methoxyfuro[2,3-c]pyridine4-carboxylic acid (3,5-dichloropyridin-4-yl)amide A solution of 4-amino-3,5-dichloropyridine (57 mg) in dry N,N-dimethylformamide (10 ml) was stirred at room temperature under an atmosphere of dry nitrogen. Sodium hydride (21 mg) was added and stirring continued for 45 minutes. 2-Acetyl-7-methoxyfuro[2,3-c]pyridine-4-carboxylic acid 4-nitrophenyl ester (100 mg) was added and the resulting mixture stirred overnight. The solvent was removed in vacuo, the residue taken up in water (100 ml) and extracted with ethyl acetate (3×100 ml). The combined organic extracts were washed with water (100 ml) then brine (50 ml), dried over magnesium sulfate, filtered and the solvent removed in vacuo. Purification by column chromatography on silica eluting with 50% hexane in ethyl acetate gave the title compound (12 mg) as a white solid.
TLC R$_f$ 0.32 (50% hexane in ethyl acetate)
m.p. 253° C. (dec.)

The following compounds were prepared in a similar manner.

EXAMPLE 2

2-Ethyl-7-methoxyfuro[2,3-c]pyridine-4-carboxylic acid (3,5-dichloropyridin-4-yl)amide Starting from 2-ethyl-7-methoxyfuro[2,3-c]pyridine-4-carboxylic acid 4-nitrophenyl ester (0.20 g) and 4-amino-3,5-dichloropyridine (0.11 g). Purification by trituration with ether gave the title compound (0.16 g) as a white solid.
TLC R$_f$ 0.51 (50% hexane in ethyl acetate)
m.p. 218–9° C.

EXAMPLE 3

2-Ethyl-7-methoxyfuro[2,3-c]pyridine-4-carboxylic acid (3-chloropyridin-4-yl)amide Starting from 2-ethyl-7-methoxyfuro[2,3-c]pyridine-4-carboxylic acid 4-nitrophenyl ester (0.20 g) and 4-amino-3-chloropyridine (0.15 g). Purification by column chromatography on silica eluting with 50% hexane in ethyl acetate gave the title compound (0.14 g) as a white solid.

TLC R$_f$ 0.42 (50% hexane in ethyl acetate)
m.p. 172–3° C.

EXAMPLE 4

7-Methoxy-2-(tetrahydropyran-4-yl)furo[2,3-c] pyridine-4-carboxylic acid (3,5-dichloropyridin-4-yl)amide Starting from 7-methoxy-2-tetrahydropyran-4-yl)furo[2,3-c]pyridine-4-carboxylic acid 4-nitrophenyl ester(0.30 g) and 4-amino-3,5-dichloropyridine (0.15 g). Purification by column chromatography on silica eluting with 50% hexane in ethyl acetate gave the title compound (0.26 g) as a white solid.
TLC R$_f$ 0.28 (50% hexane in ethyl acetate)
m.p. 222–3° C.

EXAMPLE 5

7-Methoxy-2-methoxymethylfuro[2,3-c]pyridine-4-carboxylic acid (3,5-dichloropyridin-4-yl)amide Starting from 7-methoxy-2-methoxymethylfuro[2,3-c]pyridine-4-carboxylic acid 4-nitrophenyl ester (300 mg) and 4-amino-3,5-dichloropyridine (54 mg). Purification by column chromatography on silica eluting with 1% methanol in dichloromethane gave the title compound (115 mg) as a white solid.
TLC R$_f$ 0.4 (1% methanol in dichloromethane)

EXAMPLE 6

7-Methoxy-2-methoxymethylfuro[2,3-c]pyridine-4-carboxylic acid (3,5dichloro-1-oxypyridin-4-yl)amide Starting from 7-methoxy-2-methoxymethylfuro[2,3-c]pyridine-4-carboxylic acid 4-nitro phenyl ester (200 mg) and 4-amino-3,5-dichloropyridine-N-oxide (300 mg). Purification by column chromatography on silica eluting with 5% methanol in dichloromethane gave the title compound (115 mg) as a pale yellow solid.
TLC R$_f$ 0.4 (10% methanol in dichloromethane)

EXAMPLE 7

2-Ethyl-7-methoxyfuro[2,3-c]pyridine-4-carboxylic acid (5-cyanopyrimidin-4-yl)amide Starting from 2-ethyl-7-methoxyfuro[2,3-c]pyridine-4-carboxylic acid 4-nitrophenyl ester (200 mg) and 4-aminopyrimidine-5-carbonitrile (84 mg). Purification by trituration with ethyl acetate and methanol gave the title compound (110 mg) as an off white solid.
TLC R$_f$ 0.48 (ethyl acetate)
m.p. 237–8° C.

EXAMPLE 8

2-Ethyl-7-methoxyfuro[2,3-c]pyridine-4-carboxylic acid (3-methoxypyridin-4-yl)amide Starting from 2-ethyl-7-methoxyfuro[2,3-c]pyridine-4-carboxylic acid 4-nitrophenyl ester (170 mg) and 4-amino-3-methoxypyridine (120 mg). Purification by column chromatography on silica eluting with ethyl acetate gave the title compound (0.14 g) as an off white solid.
TLC R$_f$ 0.46 (ethyl acetate)
m.p. 144–5° C.

EXAMPLE 9

7-Methoxy-2-pyridin-3-yl-furo[2,3-c]pyridine-4-carboxylic acid (3,5-dichloro-1-oxypyridin-4-yl)amide Starting from 7-methoxy-2-pyridin-3-yl-furo[2,3-c]pyridine-4-carboxylic acid 4-nitrophenyl ester (0.40 g) and 4-amino-3,5-dichloropyridine-N-oxide (0.55 g). Purification by column chromatography on silica eluting with 5% methanol in dichloromethane followed by trituration with ether gave the title compound (0.17 g) as a white solid.
TLC R$_f$ 0.28 (10% methanol in dichloromethane)
m.p. 280–282° C.

EXAMPLE 10

7-Methoxy-2-(tetrahydrofuran-3-yl)furo[2,3-c]pyridine-4-carboxylic acid (3,5-dichloro-1-oxypyridin-4-yl)amide Starting from 7-methoxy-2-(tetrahydrofuran-3-yl)furo[2,3-c]pyridine-4-carboxylic acid 4-nitrophenyl ester (0.43 g) and 4-amino-3,5-dichloropyridine-N-oxide (0.31 g). Purification by column chromatography on silica eluting with 2.5% methanol in dichloromethane increasing to 5% methanol in dichloromethane afforded the title compound as a white solid (0.265 g).
TLC R$_f$ 0.45 (10% methanol in dichloromethane)
m.p. 235–237° C.

EXAMPLE 11

4-[4-(3,5-Dichloro-1-oxypyridin-4-ylcarbamoyl)-7-methoxyfuro[2,3-c]pyridin-2-yl]-4-methoxypiperidine-1-carboxylic acid tert-butylester Starting from 2-tert-butoxycarbonyl-4-methoxypiperidin-4-yl)-7-methoxyfuro[2,3-c]pyridine-4-carboxylic acid 4-nitrophenyl ester (0.723 g) and 4-amino-3,5-dichloropyridine-N-oxide (0.737 g). Purification by column chromatography on silica eluting with 5% methanol in dichloromethane followed by preparative thin layer chromatography using 100% dichloromethane then 5% methanol in dichloromethane gave the title compound (0.014 g) as an orange solid.
TLC R$_f$ 0.42 (10% methanol in dichloromethane)
M.S. [M–H] observed

EXAMPLE 12

7-Methoxy-2-(4-methoxy-1-methylpiperidin-4-yl)furo[2,3-c]pyridine-4-carboxylic acid (3,5-dichloro-1-oxypyridin-4-yl)amide Starting from 7-methoxy-2-(4-methoxy-1-methylpiperidin-4-yl)furo[2,3-c]pyridine-4-carboxylic acid 4-nitrophenyl ester (216 mg) and 4-amino-3,5-dichloropyridine-N-oxide (263 mg). Purification by column chromatography on silica eluting with 20% methanol in dichloromethane gave the title compound (65 mg) as a white solid.
TLC R$_f$ 0.25 (20% methanol in dichloromethane)
M.S. [M+H] observed

EXAMPLE 13

7-Difluoromethoxy-2-ethylfuro[2,3-c]pyridine-4-carboxylic acid (3,5-dichloro-1-oxypyridin-4-yl)amide Starting from 7-difluromethoxy-2-ethylfuro[2,3-c]pyridine-4-carboxylic acid 4-nitrophenyl ester (100 mg) and 4-amino-3,5-dichloropyridine-N-oxide (140 mg). Purification by column chromatography on silica eluting with 5–8% methanol in dichloromethane followed by trituration in diethyl ether afforded the title compound as a white solid (58 mg).
TLC $R_f$ 0.52 (10% methanol in dichloromethane)
m.p. 262–264° C. (dec)

EXAMPLE 14

2-Acetyl-7-methoxyfuro[2,3-c]pyridine-4-carboxylic acid (3-methylpyridin-4-yl)amide 2-(1,1-Dimethoxyethyl)-7-methoxyfuro[2,3-c]pyridine-4-carboxylic acid (3-methylpyridin-4-yl)amide (0.15 g), trifluoroacetic acid (0.23 ml) and water (0.50 ml) were stirred at 50° C. in chloroform (20 ml) for 4 h. The mixture was cooled and diluted with dichloromethane (30 ml), washed with saturated sodium bicarbonate solution (30 ml) then water (30 ml), dried over magnesium sulfate, filtered and the solvent removed in vacuo to give the title compound (0.11 g) as a cream solid.
TLC $R_f$ 0.46 (5% methanol in ethyl acetate)
m.p. 195–6° C.

EXAMPLE 15

2-Ethyl-7-methoxyfuro[2,3-c]pyridine-4-carboxylic acid (3-methyl-pyridin-4-yl)amide A solution of 4-amino-3-methylpyridine (76 mg) in dry N,N-dimethylformamide (20 ml) was stirred at 0° C. under an atmosphere of dry nitrogen. Sodium bis(trimethylsilyl)amide (1.0M solution in tetrahydrofuran, 0.77 ml) was added and stirring continued at 0° C. for 10 minutes. 2-Ethyl-7-methoxyfuro[2,3-c]pyridine-4-carboxylic acid 4-nitrophenyl ester (0.20 g) was added and stirring continued at room temperature for 90 minutes. The solvent was then removed in vacuo, the residue taken up in water (100 ml) and extracted with ethyl acetate (3×75 ml). The combined organic extracts were washed with water (100 ml) then brine (50 ml), dried over magnesium sulfate, filtered and the solvent removed in vacuo. Purification by column chromatography on silica eluting with ethyl acetate followed by trituration with diethyl ether gave the title compound (66 mg) as a white solid.
TLC $R_f$ 0.36 (ethyl acetate)
m.p. 177–8° C.

The following compounds were prepared in a similar manner.

EXAMPLE 16

2-Ethyl-7-methoxyfuro[2,3-c]pyridine-4-carboxylic acid (2,4,6-trifluorophenyl)amide Starting from 2-ethyl-7-methoxyfuro[2,3-c]pyridine-4-carboxylic acid 4-nitrophenyl ester (0.20 g) and 2,4,6-trifluoroaniline (0.18 g). Purification by column chromatography on silica with 30% ethyl acetate in hexane followed by trituration with ether gave the title compound (0.068 g) as a white solid.
TLC $R_f$ 0.38 (30% ethyl acetate in hexane)
M.S. [M+H] observed

EXAMPLE 17

2-Ethyl-7-methoxyfuro[2,3-c]pyridine-4-carboxylic acid (2,6-dichloro-4-cyanophenyl)amide Starting from 2-ethyl-7-methoxyfuro[2,3-c]pyridine-4-carboxylic acid 4-nitrophenyl ester (0.10 g) and 4-amino-3,5-dichlorobenzonitrile (0.12 g). Purification by column chromatography on silica with 20% then 30% then 50% ethyl acetate in hexane to give the title compound (0.051 g) as a cream solid.
TLC $R_f$ 0.125 (20% ethyl acetate in hexane)
M.S. [M+H] observed

EXAMPLE 18

2-Ethyl-7-methoxyfuro[2,3-c]pyridine-4-carboxylic acid (2,6-difluorophenyl)amide Starting from 2-ethyl-7-methoxyfuro[2,3-c]pyridine-4-carboxylic acid 4-nitrophenyl ester (0.10 g) and 2,6-difluoroaniline (0.093 ml). Purification by column chromatography on silica with 30% ethyl acetate in hexane plus 1% ammonia solution, followed by trituration with ether gave the title compound (0.040 g) as a white solid.
TLC $R_f$ 0.27 (30% ethyl acetate in hexane plus 1% ammonia solution)
M.S. [M+H] observed

EXAMPLE 19

2-Ethyl-7-methoxyfuro[2,3-c]pyridine-4-carboxylic acid (4-cyano-2-methyl-2H-pyrazol-3-yl)amide Starting from 2-ethyl-7-methoxyfuro[2,3-c]pyridine-4-carboxylic acid 4-nitrophenyl ester (100 mg) and 5-amino-1-methyl-1H-pyrazole-4-carbonitrile (71 mg). Purification by column chromatography on silica eluting with 50% hexane in ethyl acetate followed by trituration with ether gave the title compound (17 mg) as a white solid.
TLC $R_f$ 0.20 (50% hexane in ethyl acetate)
M.S. [M+H] observed

EXAMPLE 20

2-Ethyl-7-methoxyfuro[2,3-c]pyridine-4-carboxylic acid (2-chloro-4-cyano-6-methylphenyl)amide Starting from 2-ethyl-7-methoxyfuro[2,3-c]pyridine-4-carboxylic acid 4-nitrophenyl ester (200 mg) and 4-amino-3-chloro-5-methylbenzonitrile (195 mg). Purification by column chromatography on silica eluting with 2% methanol in dichloromethane gave the title compound (92 mg) as a white solid.
TLC $R_f$ 0.52 (2.5% methanol in dichloromethane)
m.p. 201–3° C.

EXAMPLE 21

7-Difluoromethoxy-2-ethylfuro[2,3-c]pyridine-4-carboxylic acid (2,6-dichloro-4-cyanophenyl)amide Starting from 7-difluromethoxy-2-ethylfuro[2,3-c]pyridine-4-carboxylic acid 4-nitrophenyl ester (100 mg) and 4-amino-3,5-dichlorobenzonitrile (99 mg). Purification by column chromatography on silica eluting with 1% methanol in dichloromethane afforded the title compound as a white solid (12 mg).
TLC $R_f$ 0.65 (2.5% methanol in dichloromethane)
m.p. 208–210° C.

EXAMPLE 22

7-Difluoromethoxy-2-ethylfuro[2,3-c]pyridine-4-carboxylic acid (4-cyano-2-methyl-2H-pyrazol-3-yl)amide Starting from 7-difluromethoxy-2-ethylfuro[2,3-c]pyridine-4-carboxylic acid 4-nitrophenyl ester (100 mg) and 5-amino-1-methyl-1H-pyrazole-4-carbonitrile (65 mg). Purification by column chromatography on silica eluting with 2–3% methanol in dichloromethane followed by trituration with diethyl ether afforded the title compound as a white solid (50 mg).
TLC $R_f$ 0.61 (10% methanol in dichloromethane)
m.p. 240–242° C.

EXAMPLE 23

7-Difluoromethoxy-2-ethylfuro[2,3-c]pyridine-4-carboxylic acid (2-trinfluoromethylphenyl)amide Starting from 7-difluromethoxy-2-ethylfuro[2,3-c]pyridine-4-carboxylic acid 4-nitrophenyl ester (100 mg) and 2-(trifluoromethyl)aniline (0.1 ml). Purification by column chromatography on silica eluting with 20% ethyl acetate in hexane followed by trituration in methanol afforded the title compound as an off-white solid (43 mg).
TLC $R_f$ 0.63 (50% ethyl acetate in hexane)
M.S. [M+H] observed

EXAMPLE 24

2-Acetyl-7-methoxyfuro[2,3-c]pyridine-4-carboxylic acid (3-methyl-1-oxypyridin-4-yl)amide 2-Acetyl-7-methoxyfuro[2,3-c]pyridine-4-carboxylic acid (3-methylpyridin-4-yl)amide (0.10 g) and peracetic acid (36–40% solution in acetic acid, 0.05 ml) in chloroform (20 ml) were stirred overnight at room temperature. The solvent was removed in vacuo and the residue triturated with ether to give the title compound (0.10 g) as a pale yellow solid.
TLC $R_f$ 0.19 (10% methanol in ethyl acetate)
m.p. 218–9° C.
The following compounds were prepared in a similar manner.

EXAMPLE 25

2-Ethyl-7-methoxyfuro[2,3-c]pyridine-4-carboxylic acid (3,5-dichloro-1-oxypyridin-4-yl)amide Starting from 2-ethyl-7-methoxyfuro[2,3-c]pyridine-4-carboxylic acid (3,5-dichloropyridin-4-yl)amide (0.15 g). The reaction was stirred for 17 days. Purification by column chromatography on silica eluting with 5% methanol in ethyl acetate gave the title compound (84 mg) as a white solid.
TLC $R_f$ 0.30 (5% methanol in ethyl acetate)
m.p. 240° C. (dec.)

EXAMPLE 26

2-Ethyl-7-methoxyfuro[2,3-c]pyridine-4-carboxylic acid (3-chloro-1-oxypyridin-4-yl)amide Starting from 2-ethyl-7-methoxyfuro[2,3-c]pyridine-4-carboxylic acid (3-chloropyridin-4-yl)amide (0.11 g). The reaction was stirred for 8 days. The title compound (0.12 g) was obtained as a white solid.
TLC $R_f$ 0.47 (10% methanol in ethyl acetate)
m.p. 185–6° C.

EXAMPLE 27

2-Ethyl-7-methoxyfuro[2,3-c]pyridine-4-carboxylic acid (3-methyl-1-oxypyridin-4-yl)amide Starting from 2-ethyl-7-methoxyfuro[2,3-c]pyridine-4-carboxylic acid (3-methylpyridin-4-yl)amide (54 mg). The reaction was stirred for 2 days. Trituration with diethyl ether gave the title compound (55 mg) as a white solid.
TLC $R_f$ 0.10 (10% methanol in ethyl acetate)
m.p. 212–3° C.

EXAMPLE 28

7-Methoxy-2-(tetrahydropyran-4-yl)furo[2,3-c]pyridine-4-carboxylic acid (3,5-dichloro-1-oxypyridin-4-yl)amide Starting from 7-methoxy-2-tetrahydropyran-4-yl)furo[2,3-c]pyridine-4-carboxylic acid (3,5-dichloropyridin-4-yl)amide (240 mg). The reaction was stirred at 70° C. for 6 hours and at room temperature overnight. Purification by column chromatography on silica eluting with 5% methanol in ethyl acetate followed by trituration with diethyl ether gave the title compound (110 mg) as a white solid.
TLC $R_f$ 0.29 (5% methanol in ethyl acetate)
m.p. 238–9° C.

EXAMPLE 29

2-Ethyl-7-methoxyfuro[2,3-c]pyridine-4-carboxylic acid (3-methoxy-1-oxypyridin-4-yl)amide Starting from 2-Ethyl-7-methoxyfuro[2,3-c]pyridine-4-carboxylic acid (3-methoxypyridin-4-yl)amide (75 mg). The reaction was stirred for 11 days. Purification by column chromatography on silica eluting with 10% methanol in dichloromethane then 20% methanol in dichloromethane gave the title compound (20 mg) as a white solid
TLC $R_f$ 0.08 (10% methanol in ethyl acetate)
m.p. 185° C. (dec.)

EXAMPLE 30

7-Methoxy-2-(1-oxypyridin-3-yl)furo[2,3-c]pyridine-4-carboxylic acid (3,5-dichloro-1-oxypyrdin-4-yl)amide Starting from 7-methoxy-2-pyridin-3-yl-furo[2,3-c]pyridine-4-carboxylic acid (3,5-dichloro-1-oxypyridin-4-yl)amide (0.06 g). The reaction was stirred at room temperature overnight. Purification by column chromatography on silica eluting with 10% methanol in dichloromethane gave the title compound (0.018 g) as a white solid.
TLC $R_f$ 0.20 (90:10:1 dichloromethane:methanol:triethylamine)
m.p. 283–285° C.

EXAMPLE 31

7-Difluoromethoxy-2-ethylfuro[2,3-c]pyridine-4-carboxylic acid (3,5-dimethylisoxazol-4-yl)amide This Example was conducted following the procedure of Example 1, but starting from 7-difluoromethoxy-2-ethylfuro[2,3-c]pyridine-4-carboxylic acid 4-nitrophenyl ester (200 mg) and 3,5-dimethylisoxazol-4-ylamine (118 mg). Purification by column chromatography on silica eluting with 30% ethyl acetate in hexane followed by trituration in diethyl ether afforded the title compound as an off-white solid (18 mg).
TLC $R_f$ 0.38 (50% ethyl acetate in hexane)
M.S. [M–H] observed

What is claimed is:

1. A compound of formula (i)

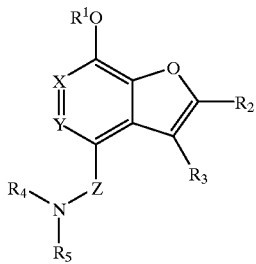

wherein X and Y are independently selected from the group consisting of CH, N and N-oxide, provided that X and Y do not both represent CH and provided that X and Y do not both represent N;

Z is CO or CS;

$R_1$ is alkyl, optionally substituted with one or more halogens;

$R_2$ is selected from the group consisting of $CF_3$, H, CN, $C(=NOR_9)R_6$, alkyl-$C(=NOR_9)R_6$, $S(O)_pR_6$, $SO_2NR_{12}R_{13}$, $CONR_{12}R_{13}$, $OR_9$, $NR_6R_{15}$; alkyl, cycloalkyl or cycloalkylalkyl optionally substituted with one or more $R_8$; aryl, heteroaryl, arylalkyl or heteroarylalkyl, the aryl/heteroaryl portions of which may be optionally substituted with one or more $R_7$ or alkyl-$R_{10}$ and the alkyl portions of which may be optionally substituted with one or more $R_8$; and heterocyclo or heterocycloalkyl, the heterocyclo portion of which may be optionally substituted with one or more $R_{11}$ or alkyl-$R_{10}$ and the alkyl portion of which may be optionally substituted with one or more $R_8$;

$R_3$ is selected from the group consisting of H, alkyl and halogen;

$R_4$ is H or alkyl;

$R_5$ is aryl or heteroaryl, optionally substituted at any position with (one or more) substituents alkyl-$R_{10}$ or $R_7$;

$R_6$ is selected from the group consisting of alkyl, aryl, heteroaryl, cycloalkyl, cycloalkylalkyl, arylalkyl, heteroarylalkyl, heterocyclo and heterocycloalkyl, the cycloalkyl/alkyl portions of which may be optionally substituted with one or more $R_8$, the aryl/heteroaryl portions of which may be optionally substituted with one or more $R_7$ or alkyl-$R_{10}$ and the heterocyclo portions of which may be optionally substituted with one or more $R_{11}$ or alkyl-$R_{10}$;

$R_7$ is alkyl or $R_{17}$;

$R_8$ is carbonyl oxygen (=O) or $R_{10}$;

$R_9$ is H or $R_6$;

$R_{10}$ is selected from the group consisting of $CO_2R_{16}$, $CONR_{12}R_{13}$, $SO_2NR_{12}R_{13}$, OH, $OR_{12}$, CN, $CF_3$, $NR_{12}R_{15}$, $COR_{12}$, $S(O)_pR_{12}$, $NHSO_2CF_3$, and $NO_2$;

$R_{11}$ is selected from the group consisting of carbonyl oxygen, alkyl and $R_{10}$;

$R_{12}$ and $R_{13}$ are the same or different and are selected from the group consisting of H, alkyl, cycloalkyl, aryl, heteroaryl, heterocyclo, cycloalkylalkyl, arylalkyl, heteroarylalkyl, and heterocycloalkyl or $NR_{12}R_{13}$ represents a heterocyclic ring, the aryl/heteroaryl portions of which may be optionally substituted with one or more $R_{18}$ and the heterocyclo portions of which may be optionally substituted with one or more $R_{19}$;

$R_{15}$ is selected from the group consisting of H, alkyl, cycloalkyl, aryl, heteroaryl, heterocyclo, cycloalkylalkyl, arylalkyl, heteroarylalkyl, heterocycloalkyl, alkylcarbonyl, alkoxycarbonyl, arylcarbonyl, heteroarylcarbonyl, heterocyclocarbonyl, alkylsulfonyl, arylsulfonyl, heteroarylsulfonyl, and heterocyclosulfonyl, the aryl/heteroaryl portions of which may be optionally substituted with one or more $R_{18}$ and the heterocyclo portions of which may be optionally substituted with one or more $R_{19}$;

$R_{16}$ is selected from the group consisting of H, alkyl, cycloalkyl, cycloalkylalkyl, arylalkyl, heteroarylalkyl, heterocyclo and heterocycloalkyl;

$R_{17}$ is halogen or $R_{10}$;

$R_{18}$ is selected from the group consisting of alkyl, alkoxy, $CF_3$, halogen, CN and $CO_2R_{16}$;

$R_{19}$ is selected from the group consisting of alkyl, alkoxy, $CF_3$, arylalkyl, carbonyl oxygen, CN or $CO_2R_{16}$; and p is 0–2;

and N-oxides and pharmaceutically-acceptable salts thereof.

2. The compound, according to claim 1, wherein Z is CO.

3. The compound, according to claim 1, wherein $R_1$ is $CH_3$ or $CHF_2$.

4. The compound, according to claim 1, wherein $R_4$ is H.

5. The compound, according to claim 1, wherein $R_5$ is selected from the group consisting of phenyl, pyrimidinyl, pyridyl, pyridyl-N-oxide, pyrazolyl, imidazolyl and isoxazolyl, any of which may be substituted at any position with (one or more) substituents $R_7$ (in which $R_7$ is alkyl optionally substituted with one or more halogens, or CN).

6. The compound, according to claim 1, wherein $R_5$ is selected from the group consisting of phenyl, pyrimidinyl, pyridyl and pyridyl-N-oxide, any of which may be substituted at any position with (one or more) substituents $R_{14}$ (in which $R_7$ is alkyl optionally substituted with one or more halogens, or CN).

7. The compound, according to claim 1, wherein X is N and Y is CH or X is CH and Y is N.

8. The compound, according to claim 1, wherein $R_2$ is alkyl or cycloalkyl optionally substituted with (one or more) $R_8$, aryl or heteroaryl optionally substituted with (one or more) $R_7$ or alkyl-$R_{10}$, or heterocyclo optionally substituted with one or more $R_{11}$ or alkyl-$R_{10}$.

9. The compound, according to claim 1, wherein $R_{10}$ is not OH or $NO_2$ and $R_{19}$ is not alkoxy.

10. The compound, according to claim 1, which is selected from the group consisting of
2-acetyl-7-methoxyfuro[2,3-c]pyridine-4-carboxylic acid (3,5-dichloropyridin-4-yl)amide,
2-acetyl-7-methoxyfuro[2,3-c]pyridine-4-carboxylic acid (3-methylpyridin-4-yl)amide, and
2-acetyl-7-methoxyfuro[2,3-c]pyridine-4-carboxylic acid (3-methyl-1-oxypyridin-4-yl)amide.

11. The compound, according to claim 1, which is selected from the group consisting of
2-ethyl-7-methoxyfuro[2,3-c]pyridine-4-carboxylic acid (3,5-dichloropyridin-4-yl)amide,
2-ethyl-7-methoxyfuro[2,3-c]pyridine-4-carboxylic acid (3,5-chloropyridin-4-yl)amide,
2-ethyl-7-methoxyfuro[2,3-c]pyridine-4-carboxylic acid (3,5-methylpyridin-4-yl)amide,
2-ethyl-7-methoxyfuro[2,3-c]pyridine-4-carboxylic acid (3,5-dichloro-1-oxypyridin-4-yl)amide,
2-ethyl-7-methoxyfuro[2,3-c]pyridine-4-carboxylic acid (3-chloro-1-oxypyridin-4-yl)amide, and 2-ethyl-7-methoxyfuro[2,3-c]pyridine-4-carboxylic acid (3-methyl-1-oxypyridin-4-yl)amide.

12. The compound, according to claim 1, which is selected from the group consisting of 7-methoxy-2-(tetrahydropyran-4-yl)furo[2,3-c]pyridine-4-carboxylic acid (3,5-dichloropyridin-4-yl)amide;

7-methoxy-2-methoxymethylfuro[2,3-c]pyridine-4-carboxylic acid (3,5-dichloropyridin-4-yl)amide;

7-methoxy-2-methoxymethylfuro[2,3-c]pyridine-4-carboxylic acid (3,5-dichloro-1-oxypyridin-4-yl)amide;

2-ethyl-7-methoxyfuro[2,3-c]pyridine-4-carboxylic acid (5-cyanopyrimidin-4-yl)amide;

2-ethyl-7-methoxyfuro[2,3-c]pyridine-4-carboxylic acid (3-methoxypyridin-4-yl)amide;

7-methoxy-2-pyridin-3-yl-furo[2,3-c]pyridine-4-carboxylic acid (3,5-dichloro-1-oxypyridin-4-yl)amide, 7-methoxy-2-(tetrahydropyran-3-yl)furo[2,3-c]pyridine-4-carboxylic acid (3,5-dichloro-1-oxypyridin-4-yl)amide;

4-[4-(3,5-dichloro-1-oxypyridin-4-ylcarbamoyl)-7-methoxyfuro[2,3-c]pyridine-2-yl)-4-methoxypiperidine-1-carboxylic acid tert-butylester, 7-methoxy-2-(4-methoxy-1-methylpiperidine-4-yl)furo[2,3-c]pyridine-4-carboxylic acid (3,5-dichloro-1-oxypyridin-4-yl)amide;

7-difluoromethoxy-2-ethylfuro[2,3-c]pyridine-4-carboxylic acid (3,5-dichloro-1-oxypyridin-4-yl)amide, 2-ethyl-7-methoxyfuro[2,3-c]pyridine-4-carboxylic acid (2,4,6-trifluorophenyl)amide, 2-ethyl-7-methoxyfuro[2,3-c]pyridine-4-carboxylic acid (2,6-dichloro-4-cyanophenyl)amide, 2-ethyl-7-methoxyfuro[2,3-c]pyridine-4-carboxylic acid (2,6-difluorophenyl)amide, 2-ethyl-7-methoxyfuro[2,3-c]pyridine-4-carboxylic acid (4-cyano-2-methyl-2H-pyrazol-3-yl)amide, 2-ethyl-7-methoxyfuro[2,3-c]pyridine-4-carboxylic acid (2-chloro-4-cyano-6-methylphenyl)amide, 7-difluoromethoxy-2-ethylfuro[2,3-c]pyridine-4-carboxylic acid (2,6-dichloro-4-cyanophenyl)amide;

7-difluoromethoxy-2-ethylfuro[2,3-c]pyridine-4-carboxylic acid (4-cyano-2-methyl-2H-pyrazol-3-yl)amide, 7-difluoromethoxy-2-ethylfuro[2,3-c]pyridine-4-carboxylic acid (2-trifluoromethylphenyl)amide, 7-methoxy-2-(tetrahydropyran-4-yl)furo[2,3-c]pyridine-4-carboxylic acid (3,5-dichloro-1-oxypyridin-4-yl)amide;

2-ethyl-7-methoxyfuro[2,3-c]pyridine-4-carboxylic acid (3-methoxy-1-oxypyridin-4-yl)amide, 7-difluoromethoxy-2-ethylfuro[2,3-c]pyridine-4-carboxylic acid (3,5-dimethylisoxazol-4-yl)amide, and 7-methoxy-2-(1-oxypyridin-3-yl)furo[2,3-c]pyridine-4-carboxylic acid (3,5-dichloro-1-oxypyridin-4-yl)amide.

13. A pharmaceutical composition for therapeutic use comprising a compound of claim 1 and a pharmaceutically-acceptable carrier or excipient.

* * * * *

UNITED STATES PATENT AND TRADEMARK OFFICE
CERTIFICATE OF CORRECTION

PATENT NO. : 6,169,090 B1
DATED : January 2, 2001
INVENTOR(S) : Dyke et al.

It is certified that error appears in the above-identified patent and that said Letters Patent is hereby corrected as shown below:

Column 30, claim 6,
Line 36, "$R_{14}$" should read -- $R_7$ --.

Signed and Sealed this

Twenty-third Day of October, 2001

Attest:

Attesting Officer

NICHOLAS P. GODICI
*Acting Director of the United States Patent and Trademark Office*